United States Patent [19]

Apelian et al.

[11] Patent Number: 5,321,194
[45] Date of Patent: Jun. 14, 1994

[54] N-OLEFIN SKELETAL ISOMERIZATION PROCESS USING DICARBOXYLIC ACID TREATED ZEOLITES

[75] Inventors: Minas R. Apelian, Vincetown; Iraj Rahmim, Turnersville, both of N.J.; Anthony S. Fung; Albin Huss, Jr., both of Chadds Ford, Pa.

[73] Assignee: Mobil Oil Corporation, Fairfax, Va.

[21] Appl. No.: 881,278

[22] Filed: May 11, 1992

[51] Int. Cl.⁵ .............................. C07C 5/27
[52] U.S. Cl. .................................. 585/671
[58] Field of Search .......................... 585/671

[56] References Cited

U.S. PATENT DOCUMENTS

| | | | |
|---|---|---|---|
| 3,442,795 | 5/1969 | Kerr et al. | 208/120 |
| 3,992,466 | 11/1976 | Plank et al. | 260/671 |
| 4,388,177 | 6/1983 | Bowes et al. | 208/111 |
| 4,886,925 | 12/1989 | Harandi | 585/331 |
| 4,922,048 | 5/1990 | Harandi | 585/310 |
| 4,996,386 | 2/1991 | Hamilton, Jr. et al. | 585/646 |
| 5,057,635 | 10/1991 | Gajda | 585/259 |

FOREIGN PATENT DOCUMENTS

| | | |
|---|---|---|
| 0026041 | 4/1981 | European Pat. Off. . |
| 0135261 | 4/1985 | European Pat. Off. . |
| 0247802 | 12/1987 | European Pat. Off. . |
| 0259526 | 3/1988 | European Pat. Off. . |
| 3246495 | 6/1984 | Fed. Rep. of Germany . |

OTHER PUBLICATIONS

Chemical Abstracts: vol. 85, No. 85: 194867m, 1976.

Primary Examiner—Asok Pal
Assistant Examiner—P. Achutamurthy
Attorney, Agent, or Firm—Alexander J. McKillop; Dennis P. Santini; Laurence P. Hobbes

[57] ABSTRACT

A method for skeletal isomerization of linear olefins to iso-olefins, e.g., n-butenes to isobutylene, over a catalyst comprising medium pore zeolite, e.g., a zeolite selected from ZSM-22, ZSM-23, and ZSM-35. Treatment of the zeolite with dicarboxylic acid, e.g., oxalic acid, significantly reduces aging rate and increases cycle length of the catalyst.

20 Claims, 1 Drawing Sheet

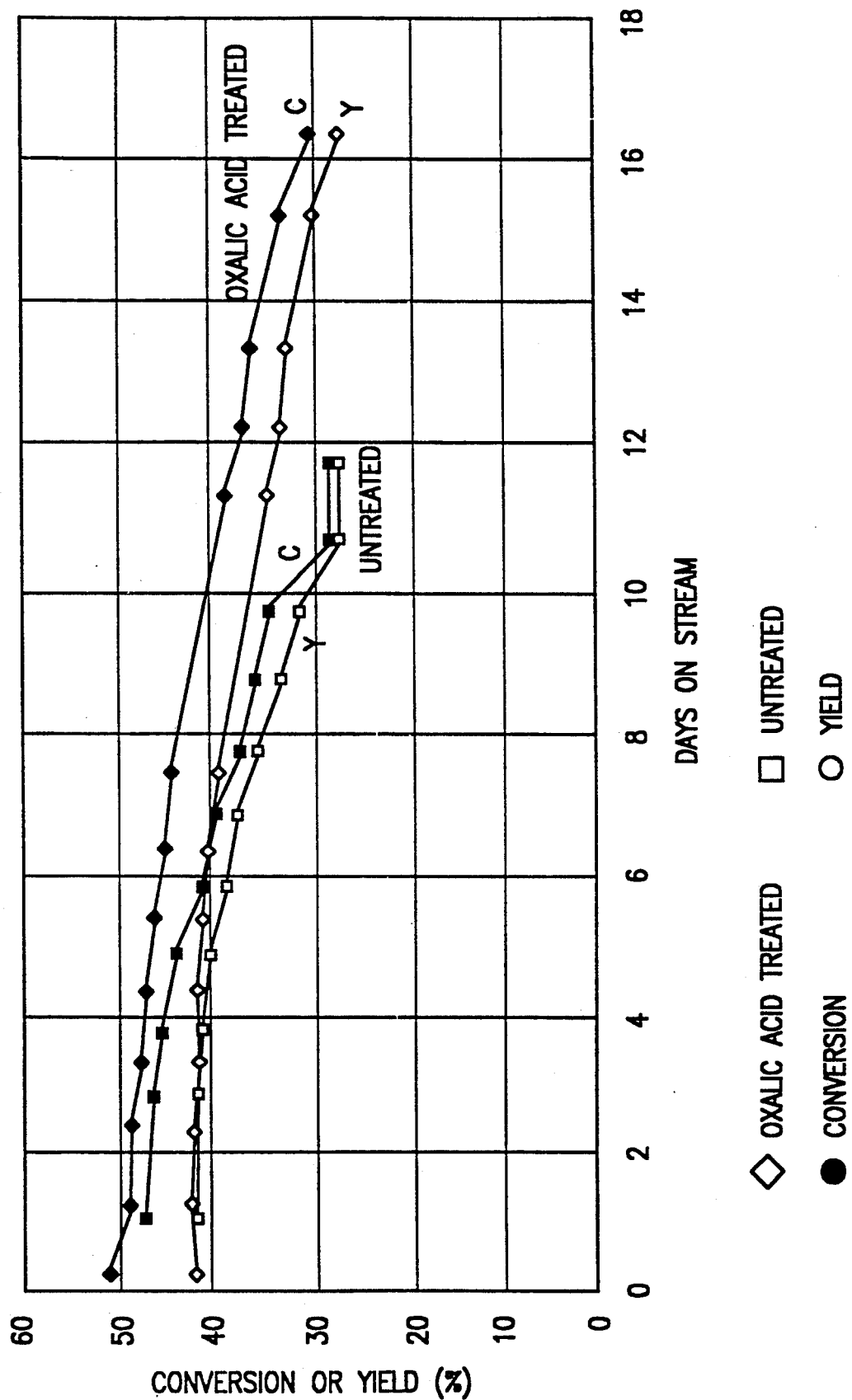

N-OLEFIN SKELETAL ISOMERIZATION PROCESS USING DICARBOXYLIC ACID TREATED ZEOLITES

Related Applications

This application is related by subject matter U.S. patent application Ser. No. 07/881,282, filed herewith, now U.S. Pat. No. 5,242,676 and Serial No. 07/760,287, filed Sept. 16, 1991, now abandoned.

FIELD OF THE INVENTION

This invention relates to a method for the skeletal isomerization of n-olefin-containing, e.g., n-butene-containing, hydrocarbon streams to iso-olefin-rich, e.g., isobutene-rich product streams. The process uses a zeolitic catalyst composition treated with dicarboxylic acid to selectively dealuminate the crystal surface of the zeolite component. The catalyst composition employed exhibits improved stability and extended cycle length.

BACKGROUND OF THE INVENTION

The demand for iso-alkenes has recently increased in response to a greater demand for oxygenated gasoline additives. For example, relatively large amounts of isobutene are required for reaction with methanol or ethanol over an acidic catalyst to produce methyl tert-butyl ether (MTBE) or ethyl tert-butyl ether (ETBE) which is useful as an octane enhancer for unleaded gasolines. Isoamylenes are required for reaction with methanol over an acidic catalyst to produce tert-amyl methyl ether (TAME). With passage of the Clean Air Act in the United States mandating increased gasoline oxygenate content, MTBE, ETBE and TAME have taken on new value as a clean-air additive, even for lower octane gasolines. Lead phasedown of gasolines in Western Europe has further increased the demand for such oxygenates.

An article by J. D. Chase, et al., *Oil and Gas Journal*, Apr. 9, 1979, discusses the advantages one can achieve by using such materials to enhance gasoline octane. The blending octane values of MTBE when added to a typical unleaded gasoline base fuel are RON=118, MON=101, R+M / 2=109. The blending octane values of TAME when added to a typical unleaded gasoline base fuel are RON=112, MON=99, R+M / 2=106. Isobutene (or isobutylene) is in particularly high demand as it is reacted with methanol to produce MTBE.

The addition of shape-selective zeolite additives such as ZSM-5 to cracking catalysts, e.g., those used in fluidized catalytic cracking (FCC), is beneficial in producing gasoline boiling range product of increased octane rating. However, increased amounts of olefins result, including n-butenes, creating a need for their conversion to higher value products such as isobutene which can be used to produce MTBE.

Butene exists in four isomers: butene-1, cis-butene-2, its stereo-isomer trans-butene-2, and isobutene. Conversions between the butenes-2 is known as geometric isomerization, whereas that between butene-1 and the butenes-2 is known as position isomerization, double-bond migration, or hydrogen-shift isomerization. The aforementioned three isomers are not branched and are known collectively as normal or n-butenes. Conversion of the n-butenes to isobutene, which is a branched isomer, is widely known as skeletal isomerization.

The reaction of tertiary olefins with alkanol to produce alkyl tertiary alkyl ether is selective with respect to iso-olefins. Linear olefins are unreactive in the acid catalyzed reaction, even to the extent that it is known that the process can be utilized as a method to separate linear and iso-olefins. The typical feedstream of FCC $C_4$ or $C_{4+}$ crackate used to produce tertiary alkyl ethers in the prior art which contains normal butene and isobutene utilizes only the branched olefin in etherification. This situation presents an exigent challenge to workers in the field to discover a technically and economically practical means to utilize linear olefins, particularly normal butene, in the manufacture of tertiary alkyl ethers.

In recent years, a major development within the petroleum industry has been the discovery of the special catalytic capabilities of a family of zeolite catalysts based upon medium pore size shape selective metallosilicates. Discoveries have been made leading to a series of analogous processes drawn from the catalytic capability of zeolites in the restructuring of olefins.

European Patent 0026041 to Garwood, incorporated herein by reference, discloses a process for the restructuring of olefins in contact with zeolite catalyst to produce iso-olefins, followed by the conversion of iso-olefins to MTBE and TAME. The restructuring conditions comprise temperatures between 204° C. and 315° C. and pressure below 51 kPa.

In European Patent 0247802 to Barri et al., it is taught that linear olefins can be restructured in contact with zeolite catalyst, including Theta-1 (ZSM-22) and ZSM-23, to produce branched olefins. The restructuring conditions comprise temperature between 200°–550° C., pressure between 100 and 5000 kPa and WHSV between 1 and 100. Selectivities to isobutene up to 91.2% are reported using a calcined Theta-1 tectometallosilicate at 400° C. and 30.6% 1-butene conversion.

U.S. Pat. No. 3,992,466 to Plank et al. teaches the use of ZSM-35 as a catalyst for hydrocarbon conversion reactions, including "isomerization of aromatics, paraffins and olefins."

U.S. Pat. No. 4,922,048 to Harandi discloses the use of a wide variety of medium pore size zeolites, e.g., ZSM-5, ZSM-11, ZSM-12, ZSM-22, ZSM-23, ZSM-35 and ZSM-48, in low temperature (232°–385° C.) olefin interconversion of $C_2$–$C_6$ olefins to products including tertiary $C_4$–$C_5$ olefins and olefinic gasoline.

U.S. Pat. No. 4,886,925 to Harandi discloses low pressure high temperature conversion of light olefins to produce higher olefins rich in isoalkenes. The process converts $C_{2+}$ n-alkenes to a product comprising $C_4$–$C_6$ alkenes rich in iso-alkenes, $C_{7+}$ olefinic gasoline boiling range hydrocarbons, and unconverted hydrocarbons over ZSM-5. The reference teaches further treatment of the alkene effluent with methanol in the presence of medium pore size zeolites such as ZSM-5, ZSM-11, ZSM-12, ZSM-35, ZSM-38 and ZSM-48.

U.S. Pat. No. 4,996,386 to Hamilton, Jr. discloses concurrent isomerization and disproportionation of hydrocarbon olefins using a ferrierite/Mo/W/$Al_2O_3$ catalyst. The catalyst exemplified produces fewer branched olefins than a comparable material free of ferrierite and the reference teaches that ferrierite-containing catalysts exhibit improved selectivity to linear olefins than conventionally prepared disproportionation catalysts.

All of the above references are incorporated herein by reference.

Despite the efforts exemplified in the above references, the skeletal isomerization of olefins, e.g., to produce isobutene, has been hampered by relatively low selectivity to isobutene perhaps owing to the reactivity of these olefins. It is further known that skeletal isomerization becomes more difficult as hydrocarbons of lower molecular weight are used, requiring more severe operating conditions, e.g., higher temperatures and lower linear olefin partial pressures.

Generally, the conversion of n-butenes to iso-butene is conducted at selectivities below 90%. In order to obtain higher selectivities, operation at high temperatures (>500° C.) and with high nitrogen feed dilution (butene partial pressure, typically less than 5 psia (34.5 kPa)) is generally required. Selectivities of greater than 90%, 95% or even 99% are highly advantageous in commercial conversion of n-butenes to isobutene in order to avoid the need to separate out materials other than n-butene from the product stream. Such high selectivities will permit direct introduction (cascading) or indirect introduction of the isomerizer effluent to an etherification zone where isobutene is reacted with alkanol to produce alkyl tert-butyl ether, e.g., MTBE. Unconverted n-butenes in the isomerizer effluent can be withdrawn either before the etherification zone or preferably, from the etherification zone effluent insofar as the etherification reaction utilizes only the isobutene component of the isomerizer stream. Unreacted n-butenes from the etherification zone effluent can be recycled to the isomerizer where they are converted to isobutene at high selectivity. If the recycle stream contains not only unconverted linear olefins, e.g., n-butenes, but also by-product such as other olefins (e.g., propylene) or paraffins, they have to be removed from the recycle stream, such as by distillation or by taking a slip stream. These removal steps are expensive and can lead to considerable loss of not only the by-products but butenes as well. These losses are larger when the by-products formed are present in higher concentration. Thus, even small improvements in the isobutene selectivity during n-butene isomerization have a major effect on the commercial viability of the process. However, high selectivities in skeletal isomerization processes have generally required low linear olefin partial pressures and high temperatures which place substantial limitations on such processes. It would, therefore, be advantageous to provide a skeletal isomerization catalyst capable of maintaining relatively high selectivity at low temperatures and high linear olefin partial pressures.

Certain medium pore size zeolites have been shown to be highly effective in skeletal isomerization of normal olefins. Such zeolites include those selected from the group consisting of zeolites having the framework structure of ZSM-22, ZSM-23, and ZSM-35.

Although such catalyst compositions exhibit adequate thermal stability and cycle length, improving such properties would be economically advantageous by extending catalyst life and reactor down time.

SUMMARY OF THE INVENTION

The present invention provides a method for highly selective conversion of linear olefins to corresponding iso-olefins of the same carbon number, e.g., n-butenes to isobutene, which comprises contacting, under skeletal isomerization conditions, a linear olefin-containing organic feedstock with a catalyst comprising a zeolite having a constraint index of 1 to 12, preferably one sorbing in its intracrystalline voids 10 mg to 40 mg 3-methylpentane at 90° C., 90 torr, per gram dry zeolite in the hydrogen form, said zeolite having been treated by contact with a dicarboxylic acid. The high selectivity of the treated catalysts employed in the present invention results in large part from isomerization occurring without significant conversion to lighter and heavier molecules. This phenomenon, it is believed, is a consequence of the pore structure of the zeolite component of the catalyst which promotes somerization at a much faster rate than the reaction by which say, butene, is converted to lighter (mostly propylene) and heavier olefins (olefin interconversion reactions). Moreover, such isomerization takes place without significant cracking of the feed or hydrogenation or dehydrogenation effects resulting in the formation of, say, n-butane or butadiene. The present invention is particularly useful in that a dicarboxylic acid treatment of the zeolite can selectively deactivate the surface acidity of the zeolite without substantially reducing the alpha value (as hereinafter described) or overall activity of the zeolite, resulting in reduced catalyst aging and longer cycle length.

DESCRIPTION OF THE FIGURE

The Figure depicts catalyst aging for oxalic acid treated and untreated silica bound ZSM-35.

DETAILED DESCRIPTION OF THE INVENTION

The present invention provides a process which converts a linear olefin-containing hydrocarbon feedstream to an iso-olefin rich product at high iso-olefin selectivity over a dicarboxylic acid-treated zeolite catalyst under skeletal isomerization conditions.

The skeletal isomerization reaction of the present invention is carried out at temperatures between 100° and 750° C.; weight hourly space velocity based on linear olefin in the feed between 0.1 and 500 WHSV; and linear olefin partial pressure between 2 and 2000 kPa. The preferred conditions are temperatures between 200° and 600° C., more preferably between 250° and 550° C., WHSV between 1 and 400, more preferably between 5 and 100; and a linear olefin partial pressure between 10 and 500 kPa, more preferably between 20 and 200 kPa. Under these conditions the conversion of linear olefin, e.g., n-butene, can be at least 10%, preferably at least 25% and more preferably at least 35%. Generally, economically feasible isomerization is maintained at n-olefin conversion levels above 25 wt %, preferably above 30 wt %.

The present invention is especially suited to processes carried out at high linear olefin to iso-olefin selectivity, e.g, at least 75% at relatively low conversion temperatures and high linear olefin partial pressures. Such processes can maintain selectivities of at least 90, 92 or 95% at a conversion temperature less than or equal to 550°, 400° or even 350° C., and linear olefin partial pressures above 2 psia (14 kPa), e.g above 5 psia (34 kPa). Zeolites used in these processes treated with dicarboxylic acid exhibit maintain substantially equivalent overall catalytic activity as measured by alpha value. However, the treated zeolites retain their operable activity (permitting overall n-olefin conversion of at least 30%) for a significantly longer period, representing a reduction in aging rate of at least 25%, preferably at least 40% or even 50%.

Preferred feedstreams include $C_4$ or $C_{4+}$ hydrocarbon feedstreams. Linear olefins suited to use in the present invention may be derived from a fresh feedstream, preferably comprising n-butenes and/or n-pentenes, or from the effluent of an iso-olefin etherification reactor which employs alkanol and $C_4$ or $C_{4+}$ hydrocarbon feedstock. Typical hydrocarbon feedstock materials for isomerization reactions according to the present invention include olefinic streams, such as cracking process light gas containing butene isomers in mixture with substantial amounts of paraffins including n-butane and isobutane. The $C_4$ components usually contain a major amount of unsaturated compounds, such as 10–40% isobutene, 20–55% linear butenes, and small amounts of butadiene. Also, $C_{4+}$ heavier olefinic hydrocarbon streams may be used, e.g., $C_4$ to $C_{10}$, preferably $C_4$ to $C_6$ olefinic hydrocarbon streams.

Catalyst

Medium pore size zeolites useful in this invention comprise intermediate pore size zeolites having a silica to alumina ratio of at least about 12 and a Constraint Index of about 1 to 12. The Constraint Index relates to zeolite pore size, and will be more fully described below. Examples of such zeolites are members of a novel class of zeolites that exhibit unusual properties and include ZSM-5, ZSM-11, ZSM-12, ZSM-22, ZSM-23, ZSM-35, and ZSM-48. Although these zeolites have unusually low alumina contents, i.e., high silica to alumina ratios, they are active for converting organic compounds. The activity is surprising since catalytic activity is generally attributed to framework aluminum atoms and/or cations associated with these aluminum atoms. These zeolites have an intracrystalline sorption capacity for normal hexane which is greater than that for water, i.e., they exhibit "hydrophobic" properties. An important characteristic of the crystal structure of this class of zeolites is that it provides constrained access to and egress from the intracrystalline free space by virtue of having an effective pore size intermediate between the small pore Linde A and the large pore Linde X, i.e., the pore windows of the structure have about a size such as would be provided by 10-membered rings of oxygen atoms. It is to be understood, of course, that these rings are those formed by the regular disposition of the tetrahedra making up the anionic framework of the crystalline aluminosilioate, the oxygen atoms themselves being bonded to the silicon or aluminum atoms at the centers of the tetrahedra. The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels.

The medium pore size zeolites referred to herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of oxygen atoms, then access to molecules of larger cross-section than normal hexane is excluded and the zeolite is not of the medium pore size type. Windows of 10-membered rings are preferred, although in some instances excessive puckering of the rings or pore blockage may render these zeolites ineffective.

Rather than attempt to judge from crystal structure whether or not a zeolite possesses the necessary constrained access to molecules larger than normal paraffins, a simple determination of the "Constraint Index", or C.I., as herein defined may be made by passing continuously a mixture of an equal weight of normal hexane and 3-methylpentane over a small sample, approximately one gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature is adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The C.I. is calculated as follows:

$$C.I. = \frac{\log (\text{fraction of n-hexane remaining})}{\log (\text{fraction of 3-methylpentane remaining})}$$

The Constraint Index approximates the ratio of the cracking rate constants for the two hydrocarbons. Zeolites suitable for the present invention are those having a Constraint Index of 1 to 12. C.I. values for some typical zeolites are:

TABLE I

| CAS | C. I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Beta | 0.6–2 |
| H-Zeolon (mordenite) | 0.4 |
| REY | 0.4 |
| Amorphous Silica-Alumina | 0.6 |
| Erionite | 38 |

The above-described Constraint Index is an important definition of zeolites which are useful in the instant invention. The very nature of this parameter and the recited technique by which it is determined, however, admit of the possibility that a given zeolite can be tested under somewhat different conditions and thereby have different Constraint Indices. Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above-specified ranges of temperature and conversion, produce a value of the Constraint Index slightly less than 1, e.g., 0.9, or somewhat greater than 12, e.g., 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove and found to have a Constraint Index of 1 to 12 is intended to be included in the instant catalyst definition regardless that the same identical zeolite tested under other defined conditions may give a Constraint Index value outside of 1 to 12.

For medium pore size zeolites of very high silica to alumina ratio, such as 1600:1, the Constraint Index cannot be measured reliably because of the low activity of the zeolite. In such cases reliance on X-ray pattern is useful.

The class of zeolites defined herein is exemplified by ZSM-5, ZSM-11, ZSM-12, ZSM-22, ZSM-23, ZSM-35, ZSM-38, ZSM-48, and other similar materials.

U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-38 is more particularly described in U.S. Pat. No. 4,046,859, the entire content of which is incorporated herein by reference.

ZSM-48 is more particularly described in U.S. Pat. No. 4,397,827, the entire content of which is incorporated herein by reference.

The specific zeolites described, when prepared in the presence of organic cations, are substantially catalytically inactive, possibly because the intra-crystalline free space is occupied by organic cations from the forming solution. These cations are removed by heating in an inert atmosphere at 1000° F. for one hour, for example, followed by base exchange with ammonium salts followed by calcination at 1000° F. in air.

The zeolites referred to above have a crystal framework density, in the dry hydrogen form, of not less than about 1.6 grams per cubic centimeter. The dry density for known crystal structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pycnometer techniques. For example, it may be determined by immersing the dry hydrogen form of the zeolite in an organic solvent not sorbed by the crystal. Or, the crystal density may be determined by mercury porosimetry, since mercury will fill th interstices between crystal but will not penetrate the intracrystalline free space.

Crystal framework densities of some typical zeolites, including some which are not within the purview of this invention, are:

TABLE II

| Zeolite | Void Volume | Framework Density |
|---|---|---|
| Ferrierite | 0.28 cc/cc | 1.76 g/cc |
| Mordenite | .28 | 1.7 |
| ZSM-5, 11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4, Omega | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

Within the above-described group of medium pore size zeolites having a constraint index of 1-12 is a preferred group of zeolites for the purposes of the present invention. The preferred members, exemplified by ZSM-22, ZSM-23, and ZSM-35, are members of a unique class of zeolites. They have channels described by 10-membered rings of T (=Si or Al) or oxygen atoms, i.e., they are intermediate pore zeolites, distinct from small pore 8-ring or large pore 12-ring zeolites. They differ, however, from other intermediate pore 10-ring zeolites, such as ZSM-5, ZSM-11, ZSM-57 or stilbite, in having a smaller 10-ring channel. If the crystal structure (and hence pore system) is known, a convenient measure of the channel cross-section is given by the product of the dimensions (in angstrom units) of the two major axes of the pores. These dimensions are listed in the "Atlas of Zeolite Structure Types" by W. M. Meier and D. H. Olson, Butterworths, publisher, Second Edition, 1987. The values of this product, termed the Pore Size Index, are listed in Table A.

TABLE A

| | | | Pore Size Index | |
|---|---|---|---|---|
| Type | Largest Ring Size | Zeolite | Axes of Largest Channel, A | Pore Size Index |
| 1 | 8 | Chabazite | 3.8 × 3.8 | 14.4 |
| | | Erionite | 3.6 × 5.1 | 18.4 |
| | | Linde A | 4.1 × 4.1 | 16.8 |
| 2 | 10 | ZSM-22 | 4.4 × 5.5 | 24.2 |
| | | ZSM-23 | 4.5 × 5.2 | 23.4 |
| | | ZSM-35 | 4.2 × 5.4 | 22.7 |
| | | ALPO-11 | 3.9 × 6.3 | 24.6 |
| 3 | 10 | ZSM-5 | 5.3 × 5.6 | 29.1 |
| | | ZSM-11 | 5.3 × 5.4 | 28.6 |
| | | Stilbite | 4.9 × 6.1 | 29.9 |
| | | ZSM-57 (10) | 5.1 × 5.8 | 29.6 |
| 4 | 12 | ZSM-12 | 5.5 × 5.9 | 32.4 |
| | | Mordenite | 6.5 × 7.0 | 45.5 |
| | | Beta (C-56) | 6.2 × 7.7 | 47.7 |
| | | Linde-L | 7.1 × 7.1 | 50.4 |
| | | Mazzite (ZSM-4) | 7.4 × 7.4 | 54.8 |
| | | ALPO$_4$-5 | 7.3 × 7.3 | 53.3 |

It can be seen that small pore, eight-ring zeolites have a Pore Size Index below about 20, the intermediate pore, 10-ring zeolites of about 20–31, and large pore, 12-ring zeolites above about 31. It is also apparent, that the 10-ring zeolites are grouped in two distinct classes; Type 2 with a Pore Size Index between about 22.7 and 24.6, and more broadly between about 20 and 26, and Type 3 with a Pore Size Index between 28.6 and 29.9, or more broadly, between about 28 and 31.

The zeolites which are especially preferred for this invention are those of Type 2 with a Pore Size Index of 20-26.

The Type 2 zeolites are distinguished from the other types by their sorption characteristics towards 3-methylpentane. Representative equilibrium sorption data and experimental conditions are listed in Table B.

Type 2 zeolites sorb in their intracrystalline voids at least about 10 mg and no greater than about 40 mg of 3-methylpentane at 90° C., 90 torr 3-methylpentane, per gram dry zeolite in the hydrogen form. In contrast, Type 3 zeolites sorb greater than 40 mg 3-methylpentane under the conditions specified.

The equilibrium sorption are obtained most conveniently in a thermogravimetric balance by passing a stream of inert gas such as helium containing the hydrocarbon with the indicated partial pressure over the dried zeolite sample held at 90° C. for a time sufficient to obtain a constant weight.

Samples containing cations such as sodium or aluminum ions can be converted to the hydrogen form by well-known methods such as exchange at temperatures between 25° and 100° C. with dilute mineral acids, or with hot ammonium chloride solutions followed by calcination. For mixtures of zeolites with amorphous material or for poorly crystallized samples, the sorption values apply only to the crystalline portion.

This method of characterizing the Type 2 zeolites has the advantage that it can be applied to new zeolites whose crystal structure has not yet been determined.

TABLE B

Equilibrium Sorption Data of Medium Pore Zeolites

| Type | Zeolite | Amount sorbed, mg per g zeolite 3-Methylpentane[a] |
|---|---|---|
| 2 | ZSM-22 | 20 |
|  | ZSM-23 | 25 |
|  | ZSM-35 | 25 |
| 3 | ZSM-5 | 61 |
|  | ZSM-12 | 58 |
|  | ZSM-57 | 70 |
|  | MCM-22 | 79 |

[a] at 90° C., 90 torr 3-methylpentane

ZSM-22 is more particularly described in U.S. Pat. No. 4,556,477, the entire contents of which are incorporated herein by reference. ZSM-22 and its preparation in microcrystalline form using ethylpyridinium as directing agent is described in U.S. Pat. No. 4,481,177 to Valyocsik, the entire contents of which are incorporated herein by reference. For purposes of the present invention, ZSM-22 is considered to include its isotypes, e.g., Theta-1, Gallo-Theta-1, NU-10, ISI-1, and KZ-2.

ZSM-23 is more particularly described in U.S. Pat. No. 4,076,842, the entire contents of which are incorporated herein by reference. For purposes of the present invention, ZSM-23 is considered to include its isotypes, e.g., EU-13, ISI-4, and KZ-1.

ZSM-35 is more particularly described in U.S. Pat. No. 4,016,245, the entire contents of which are incorporated herein by reference. Isotypes of ZSM-35 include ferrierite (P. A. Vaughan, Acta Cryst. 21, 983 (1966)); FU-9 (D. Seddon and T. V. Whitam, European Patent B-55,529, 1985); ISI-6 (N. Morimoto, K. Takatsu and M. Sugimoto, U.S. Pat. No. 4,578,259, 1986); monoclinic ferrierite (R. Gramlich-Meier, V. Gramlich and W. M. Meier, Am. Mineral. 70, 619 (1985)); NU-23 (T. V. Whittam, European Patent A-103,981, 1984); and Sr-D (R. M. Barrer and D. J. Marshall, J. Chem. Soc. 1964, 2296 (1964)). An example of a piperidine-derived ferrierite is more particularly described in U.S. Pat. No. 4,343,692, the entire contents of which are incorporated herein by reference. Other synthetic ferrierite preparations are described in U.S. Pat. Nos. 3,933,974; 3,966,883; 4,000,248; 4,017,590; and 4,251,499, the entire contents of all being incorporated herein by reference. Further descriptions of ferrierite are found in Bibby et al, "Composition and Catalytic Properties of Synthetic Ferrierite," Journal of Catalysis, 35, pages 256-272 (1974).

The zeolite catalyst used is preferably at least partly in the hydrogen form, e.g., HZSM-22, HZSM-23, or HZSM-35. Other metals or cations thereof, e.g., rare earth cations, may also be present. When the zeolites are prepared in the presence of organic cations, they may be quite inactive possibly because the intracrystalline free space is occupied by the organic cations from the forming solution. The zeolite may be activated by heating in an inert or oxidative atmosphere to remove the organic cations, e.g., by heating at over 500° C. for 1 hour or more. Other cations, e.g., metal cations, can be introduced by conventional base exchange or impregnation techniques.

The zeolite may be incorporated in another material usually referred to as a matrix or binder. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

Of all the foregoing materials, silica may be preferred as the matrix material owing to its relative inertness for catalytic cracking reactions which are preferably minimized in the instant isomerization processes. The relative proportions of finely divided zeolite and inorganic oxide gel matrix vary widely with the zeolite content ranging from about 1 to about 90 percent by weight and more usually in the range of about 30 to about 80 percent by weight of the composite.

The regeneration of spent zeolite catalyst used in the isomerization reaction is carried out oxidatively or hydrogenatively employing procedures known in the art. The catalyst of the present invention can be readily reactivated without significantly reducing selectivity for iso-olefin by exposing it to hydrogen for a suitable period, e.g., overnight.

In order to obtain desired linear olefin skeletal isomerization activity/selectivity, the zeolite, preferably in the hydrogen form, should have an alpha value of at least 1, preferably at least 10 when used in the catalyst of the present invention. Alpha value, or alpha number, of a zeolite is a measure of zeolite acidic functionality and is more fully described together with details of its measurement in U.S. Pat. No. 4,016,218, *J. Catalysis,* 6, pp. 278–287 (1966) and *J. Catalysis,* 61, pp. 390–396 (1980). The experimental conditions cited in the latter reference are used for characterizing the catalysts described herein.

The surface acidity of the catalyst can be determined by conversion of tri-tertiarybutylbenzene (TTBB), a bulky molecule that can only react with the acid sites on the zeolite crystal surface. Dealkylation of TTBB is a facile, reproducible method for measuring surface acidity of catalysts. External surface acidity can be measured exclusive of internal activity for zeolites with pore diameters up to and including faujasite. As a test reaction, dealkylation of TTBB occurs at a constant temperature in the range of from 25° to 300° C. and preferably in the range of from about 200° to 260° C.

The experimental conditions for the test used herein include a temperature of 200° C. and atmospheric pressure. The dealkylation of TTBB is carried out in a glass reactor (18 cm×1 cm OD) containing an 8 g 14/30 Vycor TM chip preheater followed by 0.1 g catalyst powder mixed with Vycor TM chips. The reactor is heated to 200° C. in 30 cc/g nitrogen for 30 minutes to remove impurities from the catalyst sample. Ten g/hr of TTBB dissolved in toluene (7% TTBB) is injected into the reactor. The feed vaporizes as it passes through the preheater and passes over the catalyst sample as vapor. After equilibrium is reached the nitrogen is switched to 20 cc/min hydrogen. The test is then run for 30 minutes with the reaction products in a cold trap.

The reaction products are analyzed by gas chromatography. The major dealkylation product is di-t-butylbenzene (DTBB). Further dealkylation to t-butylbenzene (TBB) and benzene (B) occurs but to a lesser extent.

Conversion of TTBB is calculated on a molar carbon basis. Dealkylation product weight %s are each multiplied by the appropriate carbon number ratio to convert to the equivalent amount of TTBB, i.e., DTBB×18/14, TBB×18/10 and B×18/6. These values are then used in the following conversion equation where asterisks indicate adjustment to the equivalents.

$$\% \text{ Conversion} = \frac{DTBB^* + TBB^* + B^*}{TTBB + DTBB^* + TBB^* + B^*} \times 100$$

In addition, thermal background experiments using reactors filled with Vycor TM chips only show no TTBB conversion due to Vycor TM or other reactor components.

Limiting surface acidity of the above catalysts is desirable for preventing undesired reactions on the zeolite surface which are not subject to the shape-selective constraints imposed upon those reactions occurring within the zeolite interior. However, reducing the surface acidity will generally effect a reduction in overall activity of the zeolite. The present invention relates to the treatment of the zeolite which is contacted with dicarboxylic acid under conditions resulting in a reduction in surface acidity (as measured by tri-tertiarybutylbenzene conversion) of at least 20%, preferably at least 40%, more preferably at least 50%. Such reduction of surface acidity can occur without a significant reduction in overall activity as measured by alpha test. By significant reduction in overall activity is meant a reduction in alpha value of not greater than 20%.

The surface acidity of the zeolite can be reduced by dealumination of the zeolite surface. Performance measures typically improved by dealumination include product selectivity, product quality and catalyst stability.

Conventional techniques for zeolite dealumination include hydrothermal treatment, mineral acid treatment with HCl, HNO$_3$, and H$_2$SO$_4$, and chemical treatment with SiCl$_4$ or EDTA. The treatments are limited, in many cases, in the extent of dealumination by the onset of crystal degradation and loss of sorption capacity. U.S. Pat. No. 4,419,220 to LaPierre et al discloses that dealumination of zeolite Beta via treatment with HCl solutions is limited to SiO$_2$/Al$_2$O$_3$ ratios of about 200 to 300 beyond which significant losses to zeolite crystallinity are observed.

U.S. Pat. No. 3,442,795 to Kerr et al. describes a process for preparing highly siliceous zeolite-type materials from crystalline aluminosilicates by means of a solvolysis, e.g., hydrolysis, followed by a chelation. In this process, the acid form of a zeolite is subjected to hydrolysis, to remove aluminum from the aluminosilicate. The aluminum can then be physically separated from the aluminosilicate by the use of complexing or chelating agents such as ethylenediaminetetraacetic acid or carboxylic acid, to form aluminum complexes that are readily removable from the aluminosilicate. The examples are directed to the use of EDTA to remove alumina.

EP 0 259 526 B1 discloses the use of dealumination in producing zeolite ECR-17. The preferred dealumination method involves a combination of steam treatment and acid leaching, or chemical treatments with silicon halides. The acid used is preferably a mineral acid, such as HCl, HNO$_3$ or H$_2$SO$_4$, but may also be weaker acids such as formic, acetic, oxalic, tartaric acids and the like.

U.S. Pat. No. 4,388,177 to Bowes et al. discloses the preparation of a natural ferrierite hydrocracking catalyst by treatment with oxalic acid to impart catalytic activity for converting slightly branched as well as straight chain hydrocarbons in hydrodewaxing and naphtha upgrading.

The present invention provides a process for the selective dealumination of the zeolite used in skeletal isomerization of n-olefins at the zeolite crystal surface by contacting the zeolite with dicarboxylic acid. The treatment with dicarboxylic acid is believed to remove aluminum from the crystal surface of the zeolite.

The invention therefore includes a process for the dealumination of the zeolite which comprises contacting with dicarboxylic acid for a sufficient time to effect greater than about 20, 40 or even 50% dealumination of the crystal surface.

Prior to or following contact with dicarboxylic acid, the zeolite may be composited with a porous matrix material, such as alumina, silica, titania, zirconia, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia, and silica-magnesia-zirconia. The matrix may be in the form of a cogel. The relative proportions of zeolite component and inorganic oxide gel matrix may vary widely with the zeolite content ranging from between 1 to 99, more usually 5 to 80, percent by weight of the composite.

Suitable dicarboxylic acids for use in the process of this invention include oxalic, malonic, succinic, glutaric, adipic, tartaric, maleic, phthalic, isophthalic, terephthalic, fumaric or mixtures thereof. Oxalic acid is preferred. The dicarboxylic acid may be used in solution, such as an aqueous dicarboxylic acid solution.

Generally, the acid solution has a concentration in the range from about 0.01 to about 4M. Preferably, the acid solution concentration is in the range from about 1 to about 3M.

The dicarboxylic acid is generally in a volume solution to volume catalyst ratio of at least about 1:1, preferably at least about 4:1.

Treatment time with the dicarboxylic acid solution is as long as required to provide the desired reduction in surface acidity. Generally the treatment time is at least about 10 minutes. Preferably, the treatment time is at least about 1 hour.

More than one dicarboxylic acid treatment step may be employed in the process of the present invention for enhanced deactivation of surface acidity.

The treatment temperature is generally in the range from about 32° F. to about reflux. Preferably, the treatment temperature is from about 15° C. to 93° C. (60° F. to 200° F.), and more preferably from 49° C. to 82° C. (120° F. to 180° F.).

The dicarboxylic acid treatment of this invention may also be combined with other conventional dealumination techniques, such as steaming and chemical treatment.

The following examples illustrate the process of the present invention.

EXAMPLE 1

Preparation of As-Synethsized ZSM-35

1.18 parts of aluminum sulfate (17.2% $Al_2O_3$) were added to a solution containing 9.42 parts $H_2O$ and 1.38 parts of 50% NaOH solution in an autoclave. 0.03 parts of ZSM-35 seeds and 3.20 parts of Hi-Sil precipitated silica were added with agitation, followed by 1.0 part of pyrrolidine.

The reaction mixture had the following composition, in mole ratios:

| | |
|---|---|
| $SiO_2/Al_2O_3$ | 21.5 |
| $OH^-/SiO_2$ | 0.11 |
| $H_2O/Al_2O_3$ | 13.5 |
| $R/Al_2O_3$ | 6.45 | where R=pyrrolidine. The mixture was crystallized at 105° C. for 74 hours with stirring. The ZSM-35 product was filtered, washed with deionized water, and dried at 120° C.

The chemical composition of the product was, in weight percent:

| | |
|---|---|
| $SiO_2$ | 76.7 |
| $Al_2O_3$ | 6.4 |
| Na | 0.84 |
| C | 7.26 |
| N | 2.03 |
| Ash @ 1000° C. | 85.5 | with a silica/alumina ratio for the product, in moles, of 20.3/1.

EXAMPLE 2

Preparation of Silica-Bound HZSM-35

A catalyst was prepared by dry mixing 65 parts of the as-synthesized ZSM-35 of Example 1 with 35 parts of precipitated silica, in proportion to give, after calcination, 65% ZSM-35 / 35% silica in the catalyst. A solution containing 2% NaOH (based on solids) was added to the mix to create an extrudable mull, the mix was extruded to 1/16 inch (1.6 mm) diameter and dried at 120° C. The extrudate was exchanged two times with 1N $NH_4NO_3$ solution at room temperature, rinsed with deionized water, dried at 120° C. and calcined in nitrogen for 3 hours at 538° C. It was again exchanged with 1N $NH_4NO_3$ solution two times at room temperature, dried at 120° C., and calcined in air for 9 hours at 538° C.

The resulting catalyst had an alpha activity of 102 and a surface acidity of 18. Alpha activity was measured using n-hexane, a relatively small molecule which can access the intracrystalline active sites and external sites, representing overall catalyst activity. Surface acidity was measured using tri-tertiarybutylbenzene, a bulky molecule that only reacts on the zeolite crystal surface. Surface acidity is determined in accordance with the procedure set out above.

EXAMPLE 3

Oxalic Acid Treated ZSM-35

A catalyst was prepared by treating a portion of the catalyst of Example 2 with 2M oxalic acid at 71° C. for one hour. The treated sample was washed with water, dried at 150° C., and calcined at 375° C. for 3 hours. The resulting oxalic acid treated catalyst exhibited an alpha value (activity) of 92 and a surface acidity of 10. The 10% change in alpha activity from the untreated to treated catalyst is well within the accuracy of the alpha test. However, the 45% reduction in surface acidity represents a significant decrease.

EXAMPLE 4

Preparation of ZSM-23

ZSM-23 was prepared by charging 85.5 parts water to an autoclave followed by 2.64 parts KOH solution (45% by weight), 1.0 part aluminum sulfate (17.2% $Al_2O_3$) and 0.5 parts ZSM-23 seeds (100% basis). After mixing thoroughly, 14.5 parts of Ultrasil VN3 precipitated silica (Nasilco), then 5.1 parts of pyrrolidine were added and mixed thoroughly. The autoclave was heated to 160° C. with stirring and maintained at these conditions until crystallization was complete. The product was identified as ZSM-23 by X-ray diffraction. After flashing the pyrrolidine, the slurry was cooled, washed, filtered and dried. 65 parts of the dried ZSM-23 were combined with 35 parts of $SiO_2$ (Hi-Sil, a product of PPG Industries Chemical Division, dry mulled and extruded to form 1/16 inch pellets which were dried at 120° C. The pellets were then calcined in flowing nitrogen for 2 hours at 538° C. and 3 hours in air at the same temperature. The cooled catalyst was exchanged with 1 N $NH_4NO_3$ (5 cc/g catalyst) at room temperature for one hour then washed with water. The exchange procedure was repeated and the catalyst dried at 120° C. The exchanged extrudate was then calcined at 538° C. in flowing air for 3 hours. The resulting catalyst exhibited an alpha activity of 27 and a surface acidity of 3.

EXAMPLE 5

A sample of ZSM-23 from Example 4 was treated with 2M oxalic acid at 71° C. for one hour. The treated sample was washed with water, dried at 150° C. for 8 hours, and calcined at 375° C. for 3 hours. The resulting catalyst had an alpha value of 33 and a surface acidity of 1.5. While the reduction in alpha value is within the accuracy of the alpha test, the 50% reduction in surface acidity represents a significant decrease.

EXAMPLE 6

Isomerization of 1-Butene with ZSM-35 at 400° C.

The catalysts of Examples 2 and 3 were sized to 14/24 mesh and used in butene skeletal isomerization reactions. The approximate experimental conditions were:

| | |
|---|---|
| Temperature | 400° C. |
| Pressure | 207 kPa |
| 1-Butene WHSV | 33 hr$^{-1}$ (based on active component) |
| $N_2$/Butene in feed | 1 vol/vol |

The Figure graphically depicts the respective conversions and isobutene yields obtained for treated and untreated ZSM-35. Isobutene yield from the untreated catalyst dropped from more than 40% to less than 30% in less than 11 days. However, the same drop in yield with the treated catalyst took over 16 days, representing a 40 to 50% reduction in aging rate.

While the instant invention has been described by specific examples and embodiments, there is no intent to limit the inventive concept except as set forth in the following claims.

It is claimed:

1. A method for conversion of linear olefins to corresponding iso-olefins of the same carbon number which comprises contacting a linear olefin-containing organic feedstock with a catalyst comprising a zeolite sorbing 10–40 mg 3 methylpentane at 90° C., 90 torr, per g dry zeolite in the hydrogen form, under skeletal isomerization conditions, said zeolite having been contacted with dicarboxylic acid under conditions sufficient to effect a significant reduction in surface acidity of the zeolite as determined by tri-tertiarybutylbenzene conversion without substantially reducing the overall activity of the zeolite as indicated by alpha value.

2. The method of claim 1 wherein said zeolite is selected from the group consisting of those having the framework structure of ZSM-22, ZSM-23, and ZSM-35, said dicarboxylic acid is oxalic acid, and said conversion is carried out at temperatures between about 100° and 750° C., weight hourly space velocities based on linear olefins in said feedstock between 0.1 and 500 WHSV, and linear olefin partial pressures between 2 and 2000 kPa.

3. The method of claim 1 wherein said conversion is carried out at temperatures between about 200° and 600° C., weight hourly space velocities based on linear olefin in said feedstock between 1 and 400 WHSV; and linear olefin partial pressures between 10 and 500 kPa.

4. The method of claim 1 wherein said zeolite is ZSM-22.

5. The method of claim 1 wherein said zeolite is ZSM-23.

6. The method of claim 1 wherein said zeolite is ZSM-35.

7. The method of claim 1 wherein said conversion is at least 10 wt % and has a linear olefin to iso-olefin selectivity of at least 80 wt %.

8. The method of claim 1 wherein said feedstock comprises $C_4$ to $C_{10}$ linear olefins.

9. The method of claim 1 wherein said feedstock comprises $C_4$ to $C_6$ linear olefins.

10. The method of claim 1 wherein said catalyst comprises 10 to 99 wt % of a refractory inorganic oxide binder.

11. The method of claim 1 wherein said catalyst comprises 20 to 70 wt % of a silica binder.

12. The method of claim 1 wherein said surface acidity is reduced by at least 20%.

13. The method of claim 1 wherein said surface acidity is reduced by at least 50%.

14. The method of claim 1 wherein said contacting results in less than about 10% loss of crystallinity.

15. The method of claim 1 wherein said dicarboxylic acid is an aqueous dicarboxylic acid solution.

16. The method of claim 1 wherein said dicarboxylic acid is in a concentration in the range of from about 0.01 to about 4M.

17. The method of claim 1 wherein said dicarboxylic acid is selected from the group consisting of oxalic, malonic, succinic, glutaric, adipic, maleic, phthalic, isophthalic, terephthalic, fumaric, tartaric and mixtures thereof.

18. The method of claim 1 wherein said dicarboxylic acid is oxalic acid.

19. The method of claim 1 wherein said contacting is for a time of at least about 10 minutes, at a temperature in the range of from 15° C. to 93° C. (60° F. to 200° F.).

20. A method for conversion of linear olefins to corresponding iso-olefins of the same carbon number which comprises contacting a linear olefin-containing organic feedstock with a catalyst comprising a zeolite having a Pore Size Index of 20 to 26, under skeletal isomerization conditions, said zeolite being contacted with dicarboxylic acid under conditions sufficient to effect a significant reduction in surface acidity of the zeolite as determined by tri-tertiarybutylbenzene conversion without substantially reducing the overall activity of the zeolite as indicated by alpha value.

* * * * *